United States Patent
Biadatti et al.

(10) Patent No.: US 8,362,082 B2
(45) Date of Patent: *Jan. 29, 2013

(54) BIPHENYL COMPOUND SELECTIVE AGONISTS OF GAMMA RAR RECEPTORS

(75) Inventors: Thibaud Biadatti, Opio (FR); Etienne Thoreau, Saint Vallier de Thiey (FR)

(73) Assignee: Galderma Research & Development, Biot (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/243,242

(22) Filed: Sep. 23, 2011

(65) Prior Publication Data

US 2012/0016031 A1  Jan. 19, 2012

Related U.S. Application Data

(63) Continuation of application No. 12/213,177, filed on Jun. 16, 2008, now Pat. No. 8,049,034, which is a continuation of application No. PCT/EP2006/068976, filed on Nov. 28, 2006.

(30) Foreign Application Priority Data

Dec. 15, 2005  (FR) ...................... 05 12760

(51) Int. Cl.
A01N 37/10  (2006.01)

(52) U.S. Cl. .................................... 514/568

(58) Field of Classification Search .................. None
See application file for complete search history.

(56) References Cited

U.S. PATENT DOCUMENTS 6,316,009 B1  11/2001  Bernardon et al.
8,049,034 B2 *  11/2011  Biadatti et al. ................ 562/469
2007/0021473 A1  1/2007  Biadatti et al.

FOREIGN PATENT DOCUMENTS

WO  9910308  3/1999
WO  2005056516 A1  6/2005

OTHER PUBLICATIONS

Dawson et al., "[3-(5,6,7,8-Tetrahydro-5,5,8,8-tetramethyl-2-naphthalenyl)phenyl] benzoic Acid and Heterocyclic-Bridged Analogues are Novel Retinoic Acid Receptor Subtype and Retinoid X Receptor α agonists", Bioorganic & Medicinal Chemistry Letters 10 (2000) pp. 1311-1313.

* cited by examiner

Primary Examiner — Karl J Puttlitz
(74) Attorney, Agent, or Firm — SNR Denton US LLP

(57) ABSTRACT

Biphenyl compounds having the formula (I):

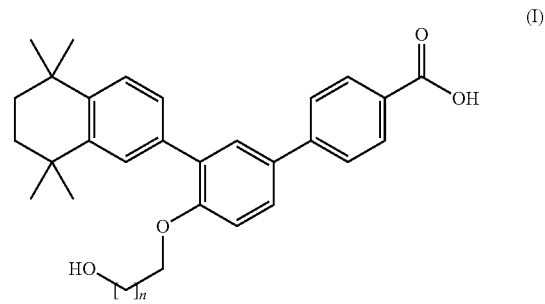

are useful for preventing/treating pathologies linked to a deficiency of the activation of the RAR gamma receptor, e.g., for treating a pathology linked to a cell differentiation and/or proliferation disorder, for treating acne, for treating psoriasis.

12 Claims, 1 Drawing Sheet

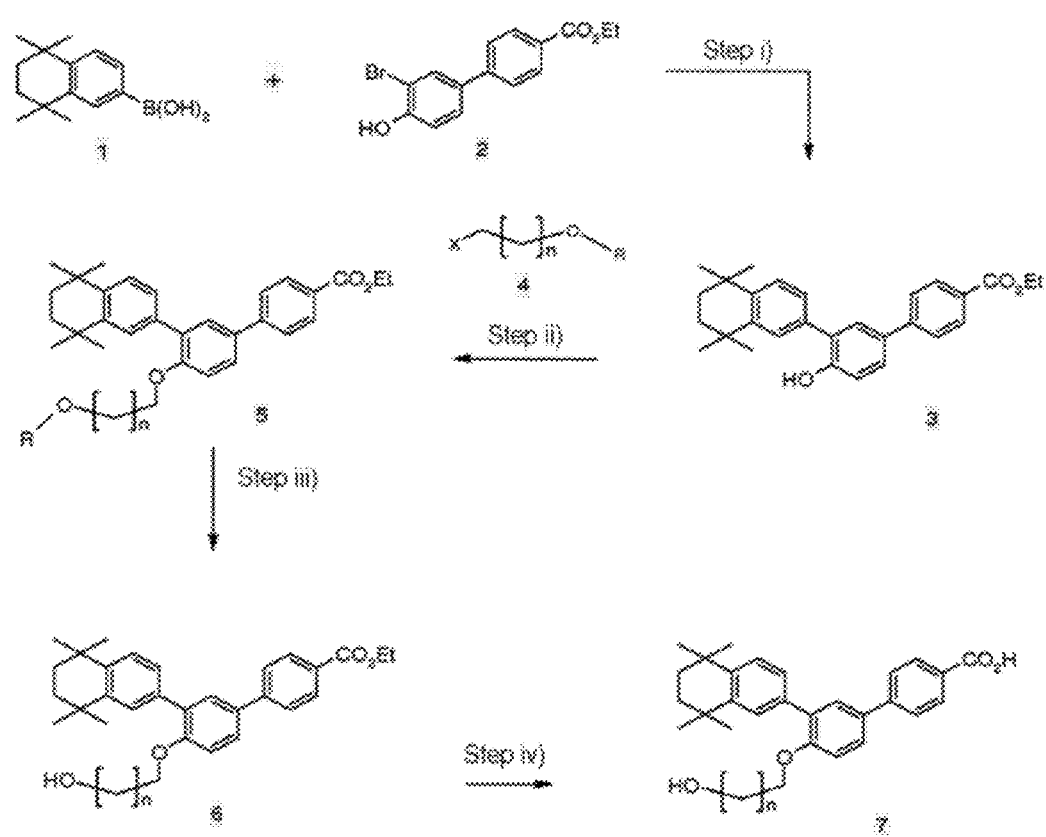

BIPHENYL COMPOUND SELECTIVE AGONISTS OF GAMMA RAR RECEPTORS

CROSS-REFERENCE TO PRIORITY/PCT APPLICATIONS

This application is a continuation of U.S. application Ser. No. 12/213,177, filed Jun. 16, 2008 and claims priority under 35 U.S.C. §119 of FR 0512760, filed Dec. 15, 2005, and is a continuation of PCT/EP 2006/068976, filed Nov. 28, 2006, and designating the United States (published in the French language on Jun. 21, 2007, as WO 2007/068580 A1; the title and abstract were also published in English), each hereby expressly incorporated by reference in its entirety and each assigned to the assignee hereof.

CROSS-REFERENCE TO COMPANION APPLICATIONS

Copending U.S. application Ser. No. 12/213,178, filed Jun. 16, 2008, hereby expressly incorporated by reference and also assigned to the assignee hereof.

BACKGROUND OF THE INVENTION

1. Technical Field of the Invention

The present invention relates to the therapeutic administration, in particular in the dermatology field, of novel biphenyl compounds substituted with an aromatic radical having selective activity for the gamma subtype of the RAR receptor family.

2. Description of Background and/or Related and/or Prior Art

A family of biphenyl compounds has been described in WO 99/10308. These compounds are described as having an application in the topical and systemic treatment of dermatological conditions linked to a keratinization disorder, and of ophthalmological conditions in particular.

The activity of these compounds has in particular been demonstrated by means of tests for differentiation of mouse embryonic teratocarcinoma F9 cells and keratinocyte differentiation tests in humans.

On the other hand, this publication in no way makes any reference to a possible specific activity of the compounds with respect to the gamma subtype of RAR receptors.

Indeed, the gamma subtype of the RAR receptor family is largely predominant in the epidermis, where it represents approximately 90% of the total receptors ("Retinoic acid receptors and binding proteins in human skin", Elder J T, Astrom A, Pettersson U, Tavakkol A, Krust A, Kastner P, Chambon P, Voorhees J. J.: *J. Invest. Dermatol.*, 1992; 98 (6 Suppl): 36S-41S; or "Retinoic acid receptor expression in human skin keratinocytes and dermal fibroblasts in vitro", Redfern C P, Todd C. J. *Cell Sci.*, 1992; 102 (Pt 1): 113-21), and it is indeed the interaction with this RAR gamma receptor which is responsible for the effectiveness of retinoids on the epidermis ("Retinoic acid receptor gamma mediates topical retinoid efficacy and irritation in animal models", Chen S, Ostrowski J, Whiting G, Roalsvig T, Hammer L, Currier S J, Honeyman J, Kwasniewski B, Yu K L, Sterzycki R, et al., *J. Invest. Dermatol.*, 1995; 104 (5): 779-83).

RAR gamma receptors are therefore the sole target in the treatment of pathologies at the epidermal level, for instance for acne or psoriasis or any other skin pathology treated with retinoids.

Furthermore, certain side effects specific to RAR alpha or RAR beta can be avoided if compounds having a selective action on RAR gamma are used.

SUMMARY OF THE INVENTION

It has now surprisingly been shown that the compounds according to the invention have an extremely advantageous selective agonist activity for the gamma subtype of the RAR receptor family.

The compounds according to the invention, selective agonists of the RAR gamma subtype, thus make it possible to prevent and/or treat various dermatological pathologies or disorders, while at the same time decreasing the side effects normally caused by the action of the active agents on the RAR alpha and beta subtypes.

The present invention therefore features compounds having the following general formula:

(I)

in which n is an integer ranging from 1 to 3 inclusive, thus equal to 1, 2 or 3, and also the salts of the compounds of formula (I).

According to a preferred embodiment, n is equal to 2 or 3, and the preferred compounds of formula (I) are selected from 4'-(3-hydroxypropoxy)-3'-(5,5,8,8-tetramethyl-5,6,7,8-tetrahydronaphthalen-2-yl)biphenyl-4-carboxylic acid and 4'-(4-hydroxybutoxy)-3'-(5,5,8,8-tetramethyl-5,6,7,8-tetrahydronaphthalen-2-yl)biphenyl-4-carboxylic acid.

The term "pharmaceutically acceptable salt" means an alkali metal salt, or an alkaline-earth metal salt, or an organic amine salt.

The present invention also features the formulation of at least one compound of formula (I), into pharmaceutical or cosmetic compositions useful in preventing and/or treating pathologies for which a selective agonist activity for the gamma subtype of the RAR receptor family is desired.

BRIEF DESCRIPTION OF THE DRAWING

The FIGURE of Drawing is a reaction scheme illustrating preparation of the compounds according to the present invention.

DETAILED DESCRIPTION OF BEST MODE AND SPECIFIC/PREFERRED EMBODIMENTS OF THE INVENTION

A general synthetic pathway for preparing the compounds of formula (I) is represented in the scheme shown in the FIGURE of Drawing.

The starting materials and/or the reactants employed are commercially available and/or can be prepared according to known methods in the literature.

According to another embodiment, the present invention also features a process for preparing the compounds of formula (I) described above, comprising the following steps:

i) coupling reaction, preferably of Suzuki reaction type, from the compound of formula 1 prepared, for example, as described in WO 99/10308:

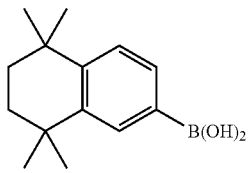

1 and the compound of formula 2 prepared, for example, as described in WO 99/10308:

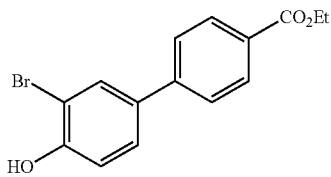

2 to produce the compound of formula 3

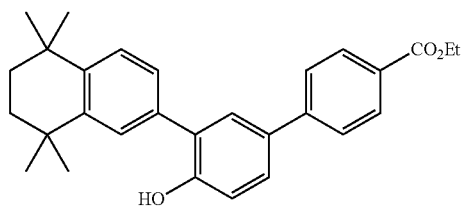

3 ii) etherification reaction, for example of the Williamson etherification type or the like (see, for example, Lerman, L et al.; *Synthesis* 2004, (18), 3043-3046), of the compound of formula 3 with the compound of formula 4,

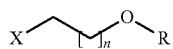

4 in which X represents a leaving group allowing a nucleophilic substitution, for instance a halogen (preferably, an iodine or bromine atom), R represents a hydrogen or a suitable protective group as described in "Protective Groups in Organic Synthesis" (Greene & Wuts, Wiley-Interscience 1991), for example acetyl or dimethyl-tert-butylsilyl, and n is an integer ranging from 1 to 3, preferably 2 or 3, to produce the compound of formula 5:

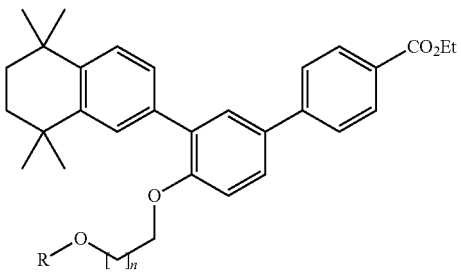

5 iii) in the case where R is other than H, this reaction ii) is followed by a reaction for deprotection of the alcohol function of the compound of formula 5, to produce the compound of formula 6:

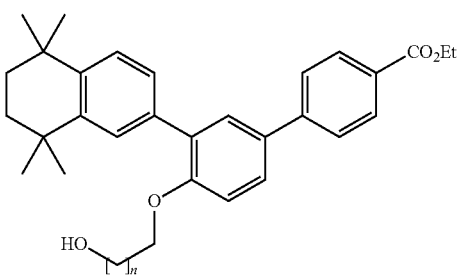

6 iv) saponification of the ester function of the compound obtained in the preceding step, i.e. step ii) for cases where R=H, or step iii) for cases where R is other than H, to produce the corresponding compound of formula (I) (compound 7 in the FIGURE of Drawing).

Step i) may, for example, be carried out in the presence of potassium carbonate and of tetrakis(triphenylphosphine)palladium in a toluene solution.

Step ii) may, for example, be carried out in the presence of cesium carbonate and of dimethylformamide and, optionally, of potassium iodide.

Step iii) may be carried out in accordance with the deprotection reactions described in "Protective Groups in Organic Synthesis" (Greene & Wuts, Wiley-Interscience 1991).

Step iv) may, for example, be carried out in the presence of sodium hydroxide and of THF.

The present invention also features administration of the compounds of formula (I) as described above, as a medicament.

According to another embodiment, this invention features pharmaceutical or cosmetic compositions, comprising, formulated into a pharmaceutically or cosmetically acceptable carrier, at least one compound of formula (I).

The term "pharmaceutically or cosmetically acceptable carrier" means a carrier suitable for use in contact with human and animal cells, with no toxicity, irritation, undue allergic response, and the like, and proportional to a reasonable advantage/risk ratio.

The administration may be carried out topically, enterally or orally, parenterally or ocularly, whether regime or regimen. Among these routes of administration, topical administration is particularly preferred.

When administered topically, the pharmaceutical compositions according to the invention are more particularly useful in the treatment of the skin and mucous membranes and may be in liquid, pasty or solid form, and more particularly in the form of salves, creams, milks, ointments, powders, impregnated pads, syndets, solutions, gels, sprays, mousses, suspensions, sticks, shampoos or washing bases. Same may also be in the form of suspensions of lipid or polymeric vesicles or microspheres or nanospheres, or polymeric or gelled patches for controlled release.

The compounds are employed topically at a concentration generally of from 0.001% and 3% by weight, relative to the total weight of the composition.

For cosmetic applications, the compositions are preferably in the form of a cream, a milk, a lotion, a gel, lipid or polymeric vesicles or microspheres or nanospheres, a soap or a shampoo.

When administered enterally or orally, the compositions may be in the form of tablets, gel capsules, sugar-coated tablets, syrups, suspensions, solutions, powders, granules, emulsions, or suspensions of lipid or polymeric vesicles or microspheres or nanospheres for controlled release. When administered parenterally, the compositions may be in the form of solutions or suspensions for perfusion or for injection.

The compounds according to the invention are generally administered at a daily dose of approximately 0.01 mg/kg to 30 mg/kg of body weight, taken in 1 to 3 doses.

The compounds of the invention can be formulated, alone or as a mixture, into pharmaceutical compositions useful in the treatment and/or prevention of pathologies linked to a deficiency in the activation of the RAR gamma receptor.

This invention also features a method of therapeutic or cosmetic treatment, comprising the administration of a pharmaceutical or cosmetic composition comprising at least one compound of formula (I), said compound exercising a selective agonist activity for the RAR gamma receptor.

The pharmaceutical compositions may be more particularly useful in treating a pathology for which the treatment requires a selective agonist activity for the RAR gamma receptor, more particularly at the level of the epithelial tissues, the skin and the bones.

The compositions can in particular be administered for the treatment of a pathology linked to cell differentiation and/or proliferation disorders, in particular in the dermatology field.

More particularly, same are useful in the treatment of a pathology linked to a keratinization disorder.

The treatment of acne is thus envisioned, in particular common acne, comedone acne, polymorphic acne, nodulocystic acne, acne conglobata, senile acne, secondary acne such as solar acne, acne medicamentosa or occupational acne.

The pharmaceutical compositions comprising a compound of formula (I) are also useful in the treatment of other dermatological conditions linked to a keratinization disorder with an inflammatory and/or immunoallergic component, and in particular all forms of psoriasis, whether cutaneous, mucosal or ungula.

The compounds according to the invention can also be formulated into cosmetic compositions, for combating skin aging, whether for example photoinduced or chronological.

The pharmaceutical or cosmetic compositions are also useful to regulate skin pigmentations and to treat actinic keratoses.

In all the applications envisioned, said compounds may be combined with another therapeutic agent that can be used in the treatment of a pathology linked to cell differentiation or proliferation disorders.

As therapeutic agents that can be included in the compositions according to the invention, exemplary are agents for modulating skin differentiation and/or proliferation and/or pigmentation, such as retinoic acid and its isomers, retinol and its esters, retinal, retinoides, estrogens, antibacterial agents, antibiotics, anti-parasitic agents, antifungal agents, steroidal or non-steroidal anti-inflammatory agents, anesthetics, anti-pruriginous agents, antiviral agents, keratolytic agents, free-radical scavengers, anti-seborrheic agents, anti-dandruff agents, anti-acne agents, agents for combating hair loss, and vitamin C and its derivatives, with the proviso, as is indicated above, that the active agents be in solubilized form in the composition according to the invention.

In order to further illustrate the present invention and the advantages thereof, the following specific examples are given, it being understood that same are intended only as illustrative and in nowise limitative. In said examples to follow, all parts and percentages are given by weight, unless otherwise indicated.

In the examples hereinafter, the samples were analyzed by $^1$H NMR, $^{13}$C NMR and HPLC/MS.

EXAMPLE 1

Synthesis of 4'-(3-hydroxypropoxy)-3'-(5,5,8,8-tetramethyl-5,6,7,8-tetrahydronaphthalen-2-yl)biphenyl-4-carboxylic acid a) Preparation of ethyl 4'-hydroxy-3'-(5,5,8,8-tetramethyl-5,6,7,8-tetrahydronaphthalen-2-yl)biphenyl-4-carboxylate 10 g (31 mmol) of ethyl 3'-bromo-4'-hydroxybiphenyl-4-carboxylate (prepared according to EP952974), 8.7 g (37 mmol) of 6-(1,1,4,4-tetramethyl-1,2,3,4-tetrahydronaphthalene)boronic acid (prepared according to EP952974) and 34 ml (74.6 mmol) of a 2M aqueous solution of potassium carbonate are placed in 200 ml of toluene, in a three-necked flask, and then 1.8 g (1.55 mmol) of tetrakis(triphenylphosphine)palladium are added under nitrogen. The reaction mixture is heated for 24 h at 110° C. After cooling, the reaction is stopped by adding 200 ml of water and then extracted with ethyl acetate. The organic phases are combined, washed with a saturated solution of sodium chloride and dried over magnesium sulfate. The solvents are evaporated off and the residue is then chromatographed on silica gel (80/20 heptane/ethyl acetate). 8 g of ethyl 4'-hydroxy-3'-(5,5,8,8-tetramethyl-5,6,7,8-tetrahydronaphthalen-2-yl)biphenyl-4-carboxylate are obtained in the form of a white solid (yield=60%).

b) Preparation of ethyl 4'-[4-(tert-butyldimethylsilanyloxy)propoxy]-3'-(5,5,8,8-tetramethyl-5,6,7,8-tetrahydronaphthalen-2-yl)biphenyl-4-carboxylate A solution of 2.1 g (4.9 mmol) of ethyl 4'-hydroxy-3'-(5,5,8,8-tetramethyl-5,6,7,8-tetrahydronaphthalen-2-yl)biphenyl-4-carboxylate is introduced into 24 ml of dimethylformamide, in a three-necked flask, and then 1.9 g (5.9 mmol) of cesium carbonate, 1.33 ml (5.9 mmol) of tert-butyl-4-iodopropoxy)dimethylsilane and 0.24 g (1.44 mmol) of potassium iodide are added. The reaction mixture is heated for 6 h at 80° C. After cooling, the reaction mixture is filtered in order to remove the cesium carbonate (rinsing with ethyl acetate). The filtrate is evaporated off under vacuum. The crude obtained in the form of an oil is chromatographed on silica gel (heptane/ethyl acetate: 95/5), to give 2.75 g of ethyl 4'-[4--

(tert-butyldimethylsilanyloxy)propoxy]-3'-(5,5,8,8-tetramethyl-5,6,7,8-tetrahydronaphthalen-2-yl)biphenyl-4-carboxylate in the form of a colorless oil (yield=93%).

c) Preparation of ethyl 4'-(3-hydroxypropoxy)-3'-(5,5,8,8-tetramethyl-5,6,7,8-tetrahydronaphthalen-2-yl)biphenyl-4-carboxylate 6.9 ml (6.9 mmol) of a solution of tetrabutylammonium fluoride (1 M) are added to a solution of 2.75 g (4.6 mmol) of ethyl 4'-[3-(tert-butyldimethylsilanyloxy)propoxy]-3'-(5,5,8,8-tetramethyl-5,6,7,8-tetrahydronaphthalen-2-yl)biphenyl-4-carboxylate in 20 ml of tetrahydrofuran, in a three-necked flask. The reaction mixture is stirred for 4 h at ambient temperature. The reaction is stopped by adding 20 ml of water and the mixture is then extracted with ethyl acetate. The organic phases are combined, washed with a saturated aqueous solution of sodium chloride, and dried over magnesium sulfate. The solvents are evaporated off. The crude obtained in the form of an oil is chromatographed on silica gel (heptane/ethyl acetate: 70/30) to give 2 g of ethyl 4'-(3-hydroxypropoxy)-3'-(5,5,8,8-tetramethyl-5,6,7,8-tetrahydronaphthalen-2-yl)biphenyl-4-carboxylate in the form of a colorless oil (yield=89%).

d) Synthesis of 4'-(3-hydroxypropoxy)-3'-(5,5,8,8-tetramethyl-5,6,7,8-tetrahydronaphthalen-2-yl)biphenylcarboxylic acid 2.05 ml (2.05 mmol) of an aqueous solution of sodium hydroxide (1 M) are added to a solution of 0.20 g (0.41 mmol) of ethyl 4'-(3-hydroxypropoxy)-3'-(5,5,8,8-tetramethyl-5,6,7,8-tetrahydronaphthalen-2-yl)biphenyl-4-carboxylate in 5 ml of tetrahydrofuran. The reaction mixture is stirred for 48 h while heating at 40° C. The reaction mixture is placed under a stream of nitrogen in order to eliminate the tetrahydrofuran and then 2.5 ml (2.5 mmol) of a solution of hydrochloric acid (1 M) are added. The product precipitates in the form of a white solid. After filtration, the product is washed twice with 5 ml of diethyl ether and then placed in an oven under vacuum overnight. 0.17 g of 4'-(3-hydroxypropoxy)-3'-(5,5,8,8-tetramethyl-5,6,7,8-tetrahydronaphthalen-2-yl)biphenyl-4-carboxylic acid is obtained (white solid, Mp=317° C., yield=90%).
$^1$H NMR (DMSO, 400 MHz): 1.26 (s, 12H); 1.6 (s, 4H); 1.90 (t, J=6.2 Hz, 2H); 3.8 (t, J=6.0 Hz, 2H); 4.09 (t, J=6.3 Hz, 2H); 7.05 (d, J=9.2 Hz, 1H); 7.25-7.29 (m, 2H); 7.50-7.52 (m, 5H); 8.01 (d, J=8.2 Hz, 2H).

EXAMPLE 2

Synthesis of 4'-(4-hydroxybutoxy)-3'-(5,5,8,8-tetramethyl-5,6,7,8-tetrahydronaphthalen-2-yl)biphenyl-4-carboxylic acid a) Preparation of ethyl 4'-[4-(tert-butyldimethylsilanyloxy)butoxy]-3'-(5,5,8,8-tetramethyl-5,6,7,8-tetrahydronaphthalen-2-yl)biphenyl-4-carboxylate A solution of 2.1 g (4.9 mmol) of ethyl 4'-hydroxy-3'-(5,5,8,8-tetramethyl-5,6,7,8-tetrahydronaphthalen-2-yl)biphenyl-4-carboxylate (prepared according to Example 1, step a) is introduced into 24 ml of dimethylformamide, in a three-necked flask, then 1.9 g (5.9 mmol) of cesium carbonate and 1.53 ml (5.9 mmol) of tert-butyl-(4-iodobutoxy)dimethylsilane are added. The reaction mixture is heated for 6 h at 80° C. After cooling, the reaction mixture is filtered in order to remove the cesium carbonate (rinsing with ethyl acetate). The filtrate is evaporated under vacuum. The crude obtained in the form of an oil is chromatographed on silica gel (heptane/ethyl acetate: 95/5), to give 2.8 g of ethyl 4'-[4-tert-butyldimethylsilanyloxy)butoxy]-3'-(5,5,8,8-tetramethyl-5,6,7,8-tetrahydronaphthalen-2-yl)biphenyl-4-carboxylate in the form of a colorless oil (yield=93%).

b) Preparation of ethyl 4'-(4-hydroxybutoxy)-3'-(5,5,8,8-tetramethyl-5,6,7,8-tetrahydronaphthalen-2-yl)biphenyl-4-carboxylate 6.8 ml (6.8 mmol) of a solution of tetrabutylammonium fluoride (1 M) are added to a solution of 2.8 g (4.5 mmol) of ethyl 4'-[4-(tert-butyldimethylsilanyloxy)butoxy]-3'-(5,5,8,8-tetramethyl-5,6,7,8-tetrahydronaphthalen-2-yl)biphenyl-4-carboxylate in 20 ml of tetrahydrofuran. The reaction mixture is stirred for 4 h at ambient temperature. The reaction is stopped by adding 20 ml of water and the mixture is then extracted with ethyl acetate. The organic phases are combined, washed with a saturated aqueous solution of sodium chloride, and dried over magnesium sulfate. The solvents are evaporated off. The crude obtained in the form of an oil is chromatographed on silica gel (heptane/ethyl acetate: 70/30), to give 2.10 g of ethyl 4'-(4-hydroxybutoxy)-3'-(5,5,8,8-tetramethyl-5,6,7,8-tetrahydronaphthalen-2-yl)biphenyl-4-carboxylate in the form of a colorless oil (yield=93%).

c) Synthesis of 4'-(4-hydroxybutoxy)-3'-(5,5,8,8-tetramethyl-5,6,7,8-tetrahydronaphthalen-2-yl)biphenyl-4-carboxylic acid 2 ml (2.0 mmol) of an aqueous solution of sodium hydroxide (1 M) are added to a solution of 0.20 g (0.40 mmol) of ethyl 4'-(4-hydroxybutoxy)-3'-(5,5,8,8-tetramethyl-5,6,7,8-tetrahydronaphthalen-2-yl)biphenyl-4-carboxylate in 8 ml of tetrahydrofuran. The reaction mixture is stirred for 48 h while heating at 40° C. The reaction mixture is placed under a stream of nitrogen in order to eliminate the tetrahydrofuran and then 2.4 ml (2.4 mmol) of a solution of hydrochloric acid (1 M) are added. The product precipitates in the form of a white solid. After filtration, the product is washed twice with 5 ml of diethyl ether and then dried in an oven under vacuum overnight. 0.17 g of 4'-(4-hydroxybutoxy)-3'-(5,5,8,8-tetramethyl-5,6,7,8-tetrahydronaphthalen-2-yl)biphenyl-4-carboxylic acid is obtained (white solid, Mp 235° C., yield=90%).
$^1$H NMR (DMSO, 400 MHz): 1.24 (s, 12H); 1.56 (m, 2H); 1.64 (s, 4H); 1.78 (m, 2H); 3.48 (t, J=6.4 Hz, 2H); 3.99 (t, J=6.5 Hz, 2H); 7.60 (d, J=8.5 Hz, 1H); 7.24-7.27 (m, 2H); 7.46-7.53 (m, 5H); 8.01 (d, J=8.3 Hz, 2H).

EXAMPLE 3

Transactivation Test

Principle of the Test:
The activation of the receptors by an agonist (activator) in HeLa cells results in the expression of a reporter gene, luciferase, which, in the presence of a substrate, generates light. It is thus possible to measure the activation of the receptors by quantifying the luminescence produced after incubation of the cells in the presence of a reference antagonist. The activating products displace the antagonist from its site, thus allowing activation of the receptor. The activity is measured by quantifying the increase in the light produced. This measurement makes it possible to determine the activator activity of the compound that can be used in the invention.

In this study, a constant which represents the affinity of the molecule for the receptor is determined. Since this value can fluctuate according to the basal activity and the expression of the receptor, it is designated apparent Kd (KdApp).

In order to determine this constant, "cross curves" of the test product (for example, 4'-(3-hydroxypropoxy)-3'-(5,5,8,8-tetramethyl-5,6,7,8-tetrahydronaphthalen-2-yl)biphenyl-4-carboxylic acid or 4'-(4-hydroxybutoxy)-3'-(5,5,8,8-tetramethyl-5,6,7,8-tetrahydronaphthalen-2-yl)biphenyl-4-carboxylic acid), against a reference antagonist otherwise known as reference ligand, 4-(5,5-dimethyl-8-p-tolyl-5,6-dihydronaphthalen-2-ylethynyl)benzoic acid, are produced. The test product is used at 10 concentrations and the reference antagonist at 7 concentrations. In each well (of a 96-well plate), the cells are in contact with one concentration of the test product and one concentration of the reference antagonist.

Measurements are also carried out for the total agonist control, otherwise known as 100% control (4-[2-(5,5,8,8-tetramethyl-5,6,7,8-tetrahydronaphthalen-2-yl)propenyl]benzoic acid), and the inverse agonist control, otherwise known as 0% control (4-{(E)-3-[4-(4-tert-butylphenyl)-5,5,8,8-tetramethyl-5,6,7,8-tetrahydronaphthalen-2-yl)]-3-oxopropenyl}benzoic acid).

These cross curves make it possible to determine the AC50 values (concentration at which 50% activation of the receptor is observed) of the reference ligand at various concentrations of test product. These AC50 values are used to calculate the Schild regression by plotting a straight line corresponding to the Schild equation ("Quantitation in receptor pharmacology" Terry P. Kenakin, Receptors and Channels, 2001, 7, 371-385).

In the case of an agonist, the AC50 is calculated by plotting the curve of the product at the concentration of the reference ligand giving 80% activation. The percentage activation which corresponds to the maximum level of activity obtained is also measured.

Materials and Method:

The HeLa cell lines used are stable transfectants containing the plasmids ERE-βGlob-Luc-SV-Neo (reporter gene) and RAR (α, β, γ) ER-DBO-puro. These cells are seeded into 96-well plates at a rate of 10 000 cells per well in 100 μl of DMEM medium without phenol red and supplemented with 10% defatted calf serum. The plates are then incubated at 37° C., 7% $CO_2$ for 4 hours.

The various dilutions of the test product, of the reference ligand (4-(5,5-dimethyl-8-p-tolyl-5,6-dihydronaphthalen-2-ylethynyl)benzoic acid), of the 100% control (100 nM 4-[2-(5,5,8,8-tetramethyl-5,6,7,8-tetrahydronaphthalen-2-yl)propenyl]benzoic acid) and of the 0% control (500 nM 4-{(E)-3-[4-(4-tert-butylphenyl)-5,5,8,8-tetramethyl-5,6,7,8-tetrahydronaphthalen-2-yl)]-3-oxopropenyl}benzoic acid) are added at a rate of 5 μl per well. The plates are then incubated for 18 hours at 37° C., 7% $CO_2$.

The culture medium is removed by turning the plates over, and 100 μl of a 1:1 PBS (phosphate buffered solution)/luciferin mixture are added to each well. After 5 minutes, the plates are read using the luminescence reader.

Results:

The values of the apparent Kd constants are indicated in the table below. These values are compared to those of the compounds of WO 99/10308 having the same activities.

| | RAR alpha Kdapp (nM) | RAR beta Kdapp (nM) | RAR gamma Kdapp (nM) |
|---|---|---|---|
| Compound of Example 1 | 15 | 4 | 0.25 |
| Compound of Example 2 | 4 | 1 | 0.03 |
| Compounds of WO 99/10308: | | | |
| 3"-Methyl-2'-(5,5,8,8-tetramethyl-5,6,7,8-tetrahydronaphthalen-2-yl)-[1,1':4,1"]-tert-phenyl-4"-carboxylic acid (Example 41) | 2 | 1 | 0.25 |
| 3"-Hydroxy-2'-(5,5,8,8-tetramethyl-5,6,7,8-tetrahydronaphthalen-2-yl)-[1,1':4,1"]-tert-phenyl-4"-carboxylic acid (Example 46) | 2 | 1 | 0.25 |
| 2"-Methoxy-2'-(5,5,8,8-tetramethyl-5,6,7,8-tetrahydronaphthalen-2-yl)-[1,1':4,1"]-tert-phenyl-4"-carboxylic acid (Example 44) | 4 | 2 | 0.5 |
| 2"-Hydroxy-2'-(5,5,8,8-tetramethyl-5,6,7,8-tetrahydronaphthalen-2-yl)-[1,1':4,1"]-tert-phenyl-4"-carboxylic acid (Example 42) | 8 | 4 | 1 |
| 6-[2-(5,5,8,8-Tetramethyl-5,6,7,8-tetrahydronaphthalen-2-yl)biphenyl-4-yl]nicotinic acid (Example 47) | 4 | 1 | 1 |
| 2'-(5,5,8,8-Tetramethyl-5,6,7,8-tetrahydronaphthalen-2-yl)-[1,1':4',1"]-tert-phenyl-4"-carboxylic acid (Example 14) | 2 | 1 | 1 |

The results obtained with 4'-(3-hydroxypropoxy)-3'-(5,5,8,8-tetramethyl-5,6,7,8-tetrahydronaphthalen-2-yl)biphenyl-4-carboxylic acid and 4'-(4-hydroxybutoxy)-3'-(5,5,8,8-tetramethyl-5,6,7,8-tetrahydronaphthalen-2-yl)biphenyl-4-carboxylic acid clearly show a better selectivity of these compounds for the gamma subtype of the RAR receptor in comparison with the other two subtypes RAR alpha and RAR beta. They also show a better activity and a better selectivity in comparison with the most active RAR compounds described in patent application WO 99/10308.

These compounds are therefore selective agonists or activators of the RAR gamma receptor.

EXAMPLE 4

Examples of Formulations

In this example, various specific formulations based on the compounds according to the invention are illustrated.

| A - ORAL ADMINISTRATION: | |
|---|---|
| (a) Tablet of 0.2 g: | |
| 4'-(3-Hydroxypropoxy)-3'-(5,5,8,8-tetramethyl-5,6,7,8-tetrahydronaphthalen-2-yl)biphenyl-4-carboxylic acid | 0.001 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |

| (b) Oral suspension in 5 ml ampoules: | |
|---|---|
| 4'-(4-Hydroxybutoxy)-3'-(5,5,8,8-tetramethyl-5,6,7,8-tetrahydronaphthalen-2-yl)biphenyl-4-carboxylic acid | 0.001 g |
| Glycerol | 0.500 g |
| 70% sorbitol | 0.500 g |
| Sodium saccharinate | 0.010 g |
| Methyl para-hydroxybenzoate | 0.040 g |
| Flavoring | qs |
| Purified water | qs 5 ml |

B - PARENTERAL ADMINISTRATION:

| (a) Composition: | |
|---|---|
| 4'-(3-Hydroxypropoxy)-3'-(5,5,8,8-tetramethyl-5,6,7,8-tetrahydronaphthalen-2-yl)biphenyl-4-carboxylic acid | 0.05% |
| Polyethylene glycol | 20% |
| 0.9% NaCl solution | qs 100 |

| (b) Injectable cyclodextrin composition: | |
|---|---|
| 4'-(4-Hydroxybutoxy)-3'-(5,5,8,8-tetramethyl-5,6,7,8-tetrahydronaphthalen-2-yl)biphenyl-4-carboxylic acid | 0.1 mg |
| β-Cyclodextrin | 0.10 g |
| Water for injectable preparation | qs 10.00 g |

C - TOPICAL ADMINISTRATION:

| (a) Ointment: | |
|---|---|
| 4'-(3-Hydroxypropoxy)-3'-(5,5,8,8-tetramethyl-5,6,7,8-tetrahydronaphthalen-2-yl)biphenyl-4-carboxylic acid | 0.300 g |
| Codex white petroleum jelly | qs 100 g |

| (b) Nonionic water-in-oil cream: | |
|---|---|
| 4'-(4-Hydroxybutoxy)-3'-(5,5,8,8-tetramethyl-5,6,7,8-tetrahydronaphthalen-2-yl)biphenyl-4-carboxylic acid | 0.100 g |
| Mixture of emulsive lanolin alcohols, of waxes and of oils ("anhydrous eucerin" sold by BDF) | 39.900 g |
| Methyl para-hydroxybenzoate | 0.075 g |
| Propyl para-hydroxybenzoate | 0.075 g |
| Sterile demineralized water | qs 100 g |

| (c) Lotion: | |
|---|---|
| 4'-(4-Hydroxybutoxy)-3'-(5,5,8,8-tetramethyl-5,6,7,8-tetrahydronaphthalen-2-yl)biphenyl-4-carboxylic acid | 0.100 g |
| Polyethylene glycol (PEG 400) | 69.900 g |
| 95% Ethanol | 30.000 g |

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for the treatment of photoinduced or chronological skin aging, for the regulation of skin pigmentations or for the treatment of actinic keratoses by selective agonist activity on the RAR gamma receptor, said method comprising administering to an individual in need of such treatment, a thus effective amount of a pharmaceutical or cosmetic composition which comprises a compound of the formula (I):

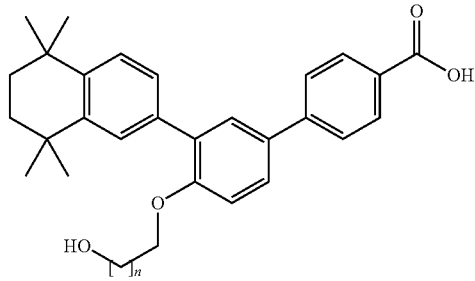

in which n is an integer ranging from 1 to 3 inclusive, or salt thereof, formulated into a pharmaceutically or cosmetically acceptable carrier.

2. The method as defined by claim 1, wherein the compound of formula (I) is 4'-(3-hydroxypropoxy)-3'-(5,5,8,8-tetramethyl-5,6,7,8-tetrahydronaphthalen-2-yl)biphenyl-4-carboxylic acid.

3. The method as defined by claim 1, wherein the compound of formula (I) is 4'-(4-hydroxybutoxy)-3'-(5,5,8,8-tetramethyl-5,6,7,8-tetrahydronaphthalen-2-yl)biphenyl-4-carboxylic acid.

4. A method for the treatment of photoinduced or chronological skin aging by selective agonist activity on the RAR gamma receptor, said method comprising administering to an individual in need of such treatment, a thus effective amount of a pharmaceutical or cosmetic composition comprising a compound of the formula (I):

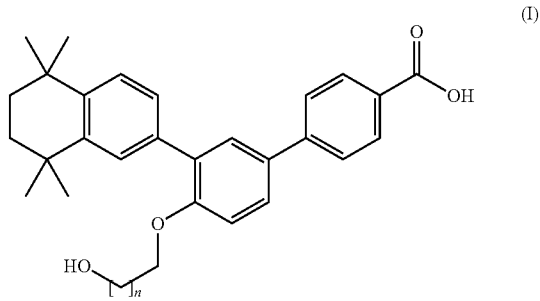

in which n is an integer ranging from 1 to 3 inclusive, or salt thereof, formulated into a pharmaceutically or cosmetically acceptable carrier.

5. The method as defined by claim 4, wherein the compound of formula (I) is 4'-(3-hydroxypropoxy)-3'-(5,5,8,8-tetramethyl-5,6,7,8-tetrahydronaphthalen-2-yl)biphenyl-4-carboxylic acid.

6. The method as defined by claim 4, wherein the compound of formula (I) is 4'-(4-hydroxybutoxy)-3'-(5,5,8,8-tetramethyl-5,6,7,8-tetrahydronaphthalen-2-yl)biphenyl-4-carboxylic acid.

7. A method for the regulation of skin pigmentations by selective agonist activity on the RAR gamma receptor, said method comprising administering to an individual in need of such treatment, a thus effective amount of a pharmaceutical or cosmetic composition comprising a compound of the formula (I):

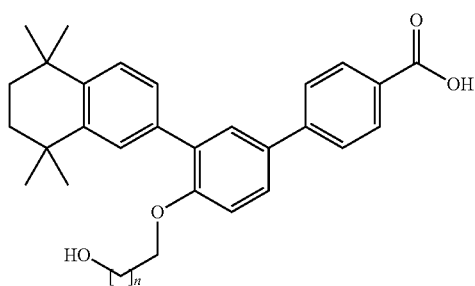

in which n is an integer ranging from 1 to 3 inclusive, or salt thereof, formulated into a pharmaceutically or cosmetically acceptable carrier.

8. The method as defined by claim 7, wherein the compound of formula (I) is 4'-(3-hydroxypropoxy)-3'-(5,5,8,8-tetramethyl-5,6,7,8-tetrahydronaphthalen-2-yl)biphenyl-4-carboxylic acid.

9. The method as defined by claim 7, wherein the compound of formula (I) is 4'-(4-hydroxybutoxy)-3'-(5,5,8,8-tetramethyl-5,6,7,8-tetrahydronaphthalen-2-yl)biphenyl-4-carboxylic acid.

10. A method for the treatment of actinic keratoses by selective agonist activity on the RAR gamma receptor, said method comprising administering to an individual in need of such treatment, a thus effective amount of a pharmaceutical or cosmetic composition comprising a compound of the formula (I):

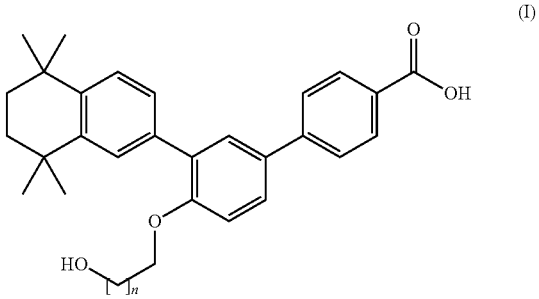

in which n is an integer ranging from 1 to 3 inclusive, or salt thereof, formulated into a pharmaceutically or cosmetically acceptable carrier.

11. The method as defined by claim 10, wherein the compound of formula (I) is 4'-(3-hydroxypropoxy)-3'-(5,5,8,8-tetramethyl-5,6,7,8-tetrahydronaphthalen-2-yl)biphenyl-4-carboxylic acid.

12. The method as defined by claim 10, wherein the compound of formula (I) is 4'-(4-hydroxybutoxy)-3'-(5,5,8,8-tetramethyl-5,6,7,8-tetrahydronaphthalen-2-yl)biphenyl-4-carboxylic acid.

\* \* \* \* \*